United States Patent [19]

Bernat et al.

[11] Patent Number: 4,977,168
[45] Date of Patent: Dec. 11, 1990

[54] DERIVATIVES OF THE N α-ARYLSULPHONYLAMINOACYL-P-AMIDINOPHENYL-ALANINAMIDES, AND THEIR USE AS MEDICAMENTS

[75] Inventors: André Bernat, Cugnaux; Denis Delabassee, Portet/Garonne; Daniel Frehel, Toulouse; Jean-Pierre Maffrand, Portet/Garonne; Eric Vallee, Tournefeuille, all of France

[73] Assignee: Sanofi, Paris, France

[21] Appl. No.: 6,152

[22] Filed: Jan. 23, 1987

[30] Foreign Application Priority Data

Jan. 24, 1986 [FR] France ................................ 86 01398
Jan. 24, 1986 [FR] France ................................ 86 01400

[51] Int. Cl.$^5$ .................... A61K 31/40; A61K 31/445; A61K 31/495; C07D 207/09; C07D 213/53; C07D 239/04
[52] U.S. Cl. .................... 514/330; 514/255; 514/423; 544/390; 548/530; 548/536; 546/319
[58] Field of Search .............................. 546/226, 319, 514/330, 423, 255, 548/530, 536; 544/390

[56] References Cited

PUBLICATIONS

B. Voigt and G. Wagner, Pharmazie 40 (1985) II 5, pp. 305–306, English Translation.
Thrombosis Research 39; 771–775, 1985; J. Hauptmann, Bridgitte Kaiser and F. Markwardt; Anticoagulant Action of Synthetic Tight Binding Inhibitors of Thrombin in Vitro and In Vivo.
Thrombosis Research 29; 635–642, 1983; J. Sturzebecher, F. Markwardt, B. Voight, G. Wagner and P. Walsmann; Cyclic Amides of Nα-Arylsulfonylaminoacylated 4-Amidinophenylalanine-Tight.
Guenther Wagner et al., Chemical Abstracts, vol. 98, 1983, p. 645, No. 107770b, Columbus, Ohio.
J. Stuerzebecher et al., "Cyclic Amides of Nα-arylsulfonylaminoiacylated 4-amidinophenylalanine-Light Binding Inhibitors of Thrombin", Chemical Abstracts, vol. 99, 1983, p. 279, No. 18600z, Columbus, Ohio.
U. Griessbach et al., "Assay of Hirudin in Plasma Using a Chromogenic Thrombin Substrate", Chemical Abstracts, vol. 102, 1985, p. 229, No. 91802b, Columbus, Ohio.
J. Hauptmann et al., "Anticoagulant Action of Syntheric Tight Binding Inhibitors of Thrombin in Viro and in Vivo", Chemical Abstracts, vol. 104, 1986, p. 43, No. 475z, Columbus, Ohio.
B. Kaiser et al., "Pharmacological Characterization of a New Highly Effective Synthetic Thrombin Inhibitor", vol. 104, 1986 p. 31, No. 45508d, Columbus, Ohio.
B. Voigt et al., Diepharmazie "Synthese vom Nalpha-Benzyloxycarbonyl-4-amidinophenylalaninamiden als Thrombininhibitoren", vol. 40, No. 5, May 1985, pp. 305–306, Berlin Germany, C.A. vol. 102, 1985 p. 735 Abst. #25017y.

*Primary Examiner*—David B. Springer
*Attorney, Agent, or Firm*—Wegner, Cantor, Mueller & Player

[57] ABSTRACT

Nα-substituted derivatives of Nα-arylsulphonylaminoacyl p-amidinophenylalaninamides, their preparation, their use as medicaments and intermediates for their synthesis.

19 Claims, No Drawings

DERIVATIVES OF THE N α-ARYLSULPHONYLAMINOACYL-P-AMIDINOPHENYL-ALANINAMIDES, AND THEIR USE AS MEDICAMENTS

SUMMARY OF THE TECHNICAL CONTENT OF THE INVENTION

The present invention concerns compounds with the formula:

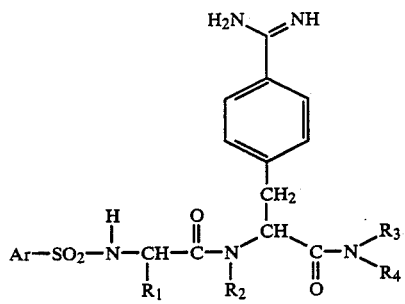

in which:

$R_1$ represents hydrogen, a lower alkyl group, a lower hydroxyalkyl group, a benzyl group, a phenyl group or a 4-hydroxyphenyl group;

$R_2$ represents a lower alkyl, lower alkenyl, lower alkynyl or benzyl group, or a lower alkoxycarbonylalkyl, lower carboxyalkyl, or lower hydroxyalkyl group;

$R_3$ and $R_4$, identical or different, each represents a lower alkyl or lower hydroxyalkyl radical, lower alkenyl or lower alkynyl radical or form together with the nitrogen to which they are attached, a saturated heterocycle such as morpholino, thiomorpholino, pyrrolidino not substituted or substituted by an alkoxycarbonyl or carboxy group, piperazino, 4-(lower alkyl)piperazino, 4-(lower hydroxyalkyl)piperazino, or piperidino not substituted or substituted by one of the following groups:- lower alkyl, benzyl, hydroxy, lower hydroxyalkyl, amino, lower aminoalkyl, hydroxyamino, alkoxycarbonyl or carboxy.

Ar represents a phenyl, alpha-naphthyl or beta-naphthyl group, possibly substituted, or a heteroaryl group chosen from the radicals pyridyl, quinolinyl, or isoquinolinyl, possibly substituted, as well as their isomers and their mixtures and their salts with pharmaceutically acceptable mineral or organic acids.

The invention also concerns a preparation process for products with the formula (I), their use as medicaments and the intermediate compounds for their synthesis.

The present invention relates to new Nα-substituted derivatives of Nα-arylsulphonylaminoacyl p-amidinophenylalaninamides, to their preparation process and to their use as selective inhibiting agents for thrombin and antithrombotics.

The compounds of the invention answer to the general formula (I):

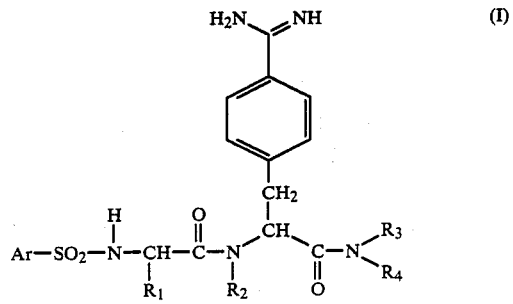

in which:

$R_1$ represents hydrogen, a lower alkyl group, a lower hydroxyalkyl group, a benzyl group, a phenyl group or a 4-hydroxyphenyl group;

$R_2$ represents a lower alkyl, lower alkenyl, or lower alkynyl group, or a benzyl group, or a lower alkoxycarbonylalkyl, lower carboxyalkyl or lower hydroxyalkyl group;

$R_3$ and $R_4$, identical or different, each represents a lower alkyl or lower hydroxyalkyl radical, lower alkenyl or lower alkynyl radical or form together with the nitrogen to which they are attached, a saturated heterocycle such as morpholino, thiomorpholino, pyrrolidino not substituted or substituted by an alkoxycarbonyl or carboxy group, piperazino, 4-(lower alkyl)piperazino, 4-(lower hydroxyalkyl)piperazino, or piperidino not substituted or substituted by one of the following groups:- lower alkyl, benzyl, hydroxy, lower hydroxyalkyl, amino, lower aminoalkyl, hydroxyamino, alkoxycarbonyl or carboxy.

Ar represents a phenyl, alpha-naphthyl or beta-naphthyl group, possibly substituted, or a heteroaryl group chosen from the radicals pyridyl, quinolinyl, or isoquinolinyl, possibly substituted.

The compounds with the formula (I), preferred above, are those in which $R_1$ represents hydrogen or an alkyl or hydroxyalkyl radical, those in which $R_2$ represents an alkyl radical, those in which the

group represents a piperidino radical, substituted or not substituted, and those in which Ar represent a naphthyl radical.

In the case where $R_1$ is other than hydrogen, the carbon carrier of the $R_1$ group, like that of the phenylalanine group, can have R or S or RS configuration, and for these latter compounds, crystallization can involve an enriching of some of the diastereoisomers. All the compounds presenting the said configurations are included in the present invention.

The compounds with the formula (I) above, containing one or more asymmetric centres, can exist in the forms of several isomers (diastereoisomers, enantiomers) which can be prepared by stereospecific synthesis or separated from their homologues by standard methods. The invention also concerns the addition salts of compounds with the formula (I) with pharmaceutically acceptable mineral or organic acids.

The terms "lower alkyl", "lower alkenyl" and "lower alkynyl" as used here, denote radicals of branched or linear aliphatic hydrocarbons, containing up to 6 carbon atoms, such as methyl, ethyl, isopropyl, isobutyl, tertbutyl, n-hexyl, allyl, propargyl, crotyl, 2-methylcrotyl, 2-methylallyl, and 2-butyryl.

Some synthetic inhibitors of thrombin, presenting an amidinophenylalanine group, have been described in the literature.

G. WAGNER and his colleagues (DD Patent No. 142804 (16.7.80)) have described compounds with the general formula (A):

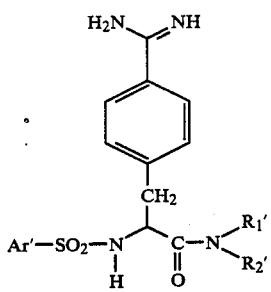

(A)

The insertion of a glycine aminoacid residue between the sulphonyl group and the N-alpha nitrogen of p-amidinophenylalanine has led to compounds with the general formula (B), whose in vitro activity is potentialized by comparison with those with the general formula (A) (G. WAGNER et coll. DD Patent No. 155954 (3.2.81),

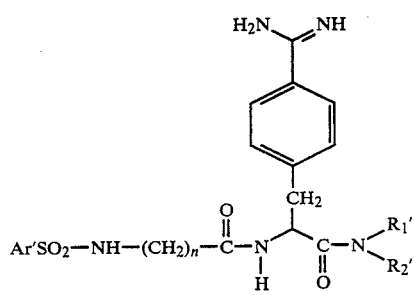

(B)

and among these, the compound with the formula (B) where n=1, A'r=beta-naphthyl, NR'$_1$R'$_2$=piperidino, hereafter denoted compound (C), shows the best inhibiting activity of thrombin in vitro (J. STRUZE-BECHER et al. Thrombosis Research, 1983, 29, 635) and ex vivo (J. HAUPTMANN et al. Thrombosis Research, 1985, 39, 771).

The compounds with the general formulae (A) and (B) above are prepared according to the processes described in patent Nos. DD 142804 and DD 155954, the amides being obtained starting from the corresponding free acids by activation and reaction with the corresponding amine. These processes involve reaction conditions which induce racemizations at the asymmetric centre; in addition, they do not allow compounds carrying substituent R$_2$ to be obtained.

The applicant has found that the compounds with the formula (I) above can be obtained by a process which allows, by the use of coupling processes and protector groups, judiciously chosen, the centres of asymmetry to be retained in their original configuration, and which does not induce racemization.

This result is obtained, contrary to the processes described by G. WAGNER and his colleagues, by first constructing the amide part

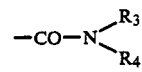

starting from the acid function of synthon-p-cyanophenylalanine, before the arylsulphonylaminoacyl part, in order to be able to introduce substituent R$_2$ easily.

The subject of the invention is also a preparation process for compounds with the formula (I) characterized in that on Nα-alkylated 4-cyanophenylalaninamide with the formula (II):

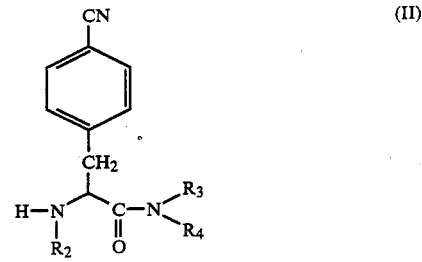

(II)

in which R$_2$, R$_3$ and R$_4$ have the same significances as in formula (I), an acid is made to react, with the formula:

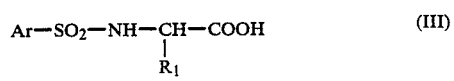

(III)

in its activated form:

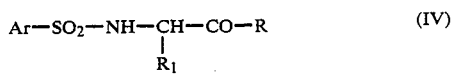

(IV)

in which Ar and R$_1$ have the same significances as in formula (I) and R represents a good nucleofuge group, such as chloro, alkoxycarbonyloxy or heteroaryl, so as to obtain the compound with the formula (V):

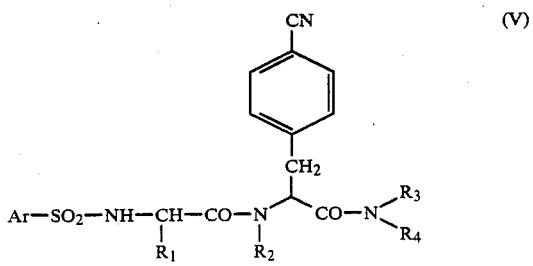

(V)

in which Ar, R$_1$, R$_2$, R$_3$ and R$_4$ have the same significances as in formula (I), which is treated with an excess of a saturated solution of hydrogen chloride gas in an alcohol with the formula X-OH in which X represents a lower alkyl radical, so as to obtain the compound with the formula (VI) in the hydrochloride form,

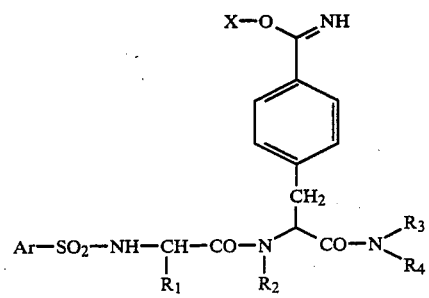

in which Ar, $R_1$, $R_2$, $R_3$, $R_4$ and X have the same previously given significances. The imidoester with the formula (VI) is then treated by an excess of a solution of ammonia in a lower alcohol at the boiling point of the reactional mixture so as to obtain the sought compound with the formula (I).

This compound is isolated in the form of a salt, the free base being able to be obtained by standard processes and possibly converted into another pharmaceutically acceptable salt such as for example, in addition to the hydrochloride, hydrobromide, sulphate, methanesulphonate, 2-naphthalenesulphonate, maleate, fumarate, citrate, acetate, gluconate, dobesilate, and sultosilate.

The preparation of the new compound with the formula (II) takes place starting from 4-cyanophenylalanine with the formula:

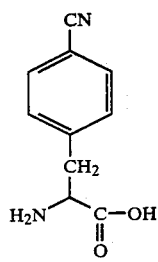

The acid with the formula:

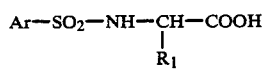

has been prepared according to the reactional scheme:

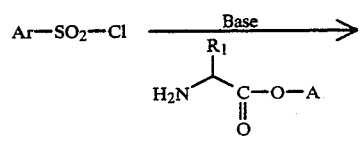

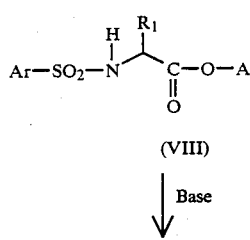

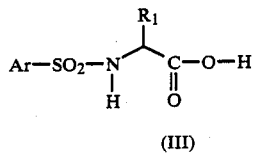

The introduction of an asymmetric centre in the aminoester (VII, A=lower alkyl) whose initial "R" or "S" configuration must be kept up to the acid (III), makes the use of non-racemizing methods necessary; such as for example:

the sulphonylation of the aminoester (VII) takes place in a two-phase medium, preferably one of the following mixtures:- water-dichloromethane, water-chloroform, or water-carbon tetrachloride, in the presence of a base, preferably an alkaline carbonate such as potassium carbonate, or sodium carbonate, at temperatures between 10° C. and 25° C.

the saponification of the ester (VIII) takes place in a hydroalcohol medium such as water-methanol or water-ethanol, in the presence of an equivalent of alkaline hydroxide, preferably sodium hydroxide, at temperatures between 10° C. and 25° C. The neutralization of the reactional medium by addition of an equivalent of a 1N aqueous solution of mineral acid, preferably hydrochloric acid, leads to acid (III). This saponification can also be carried out in a hydro-organic medium, such as water-dioxan in the same conditions.

For the conversion of the acid with the formula (III) into an activated ester with the formula (IV), there are 2 cases to consider:

(a) Case where $R_1$=H, and those in which the problem of racemization of acid (III) does not exist (non-stereospecific method)

The activation of the acid function of the synthon can be used indifferently for example by:

conversion of the acid function into an acyl halogenide (VI: R=Cl)

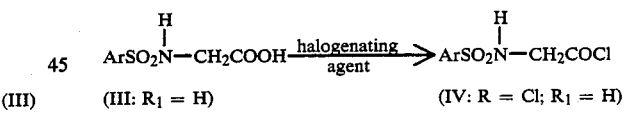

according to the process described in patent DDR No. 155954.

conversion of the acid function into mixed carbonic anhydride (IV: R = O—C(=O)—OY$_1$) according to the reactional scheme:

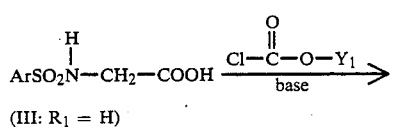

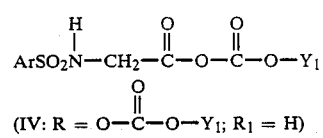

The reaction uses an alkyl chloroformate

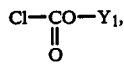

where $Y_1$ is a branched or unbranched lower alkyl radical, in the presence of a tertiary amine as a base. The alkyl chloroformate preferably used is ethyl chloroformate ($Y_1=C_2H_5$) or isobutyl chloroformate ($Y_1=CH_2-CH(CH_3)_2$). The preferred tertiary amine is triethylamine. This condensation takes place preferably at temperatures between $-5°$ C. and $+10°$ C., in an inert solvent such as dichloromethane, chloroform or carbon tetrachloride.

(b) Case where $R_1 \ne H$: when it is desired to avoid a racemization at the carbon carrier of substituent $R_1$ (stereospecific method)

The conversion of the acid function of compounds with the formula (III) into activated esters, leads to compounds with the general formula (IV: R=O-Z) according to the reactional scheme:

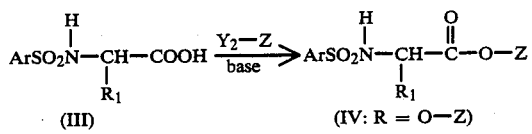

The coupling reagents $Y_2$-Z, not inducing racemization, preferably used, but non-limitative, are the following:

1-hydroxybenzotriazol (HOBT)

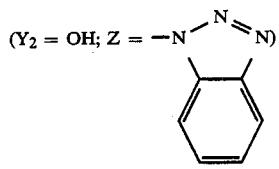

in the presence of N,N-dicyclohexylcarbodiimide (DCC) according to the operating method described by E. C. JORGENSEN et al. (J. Am. Chem. Soc. 1971, 93, 6318).

1-benzotriazolyl oxytris(dimethylamino)phosphonium hexafluorophosphate (BOP)

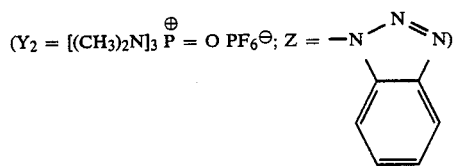

according to the operating method described by B. CASTRO et al. (Synthesis 1976, 751).

N,N-bis(2-oxo-3-oxazolidinyl)phosphorodiamide chloride

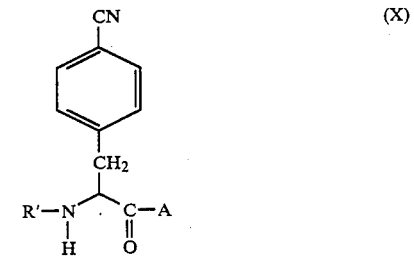

according to the operating method described by D. H. RICH et al. (J. Am. Chem. Soc. 1985, 107, 4342).

The activation and coupling reactions take place in the presence of tertiary amines, preferably triethylamine, in an inert solvent such as dichloromethane, dimethylformamide or acetonitrile, at temperatures between 15° C. and 40° C.

The formation of the imidoester (VI) takes place in an alcoholic medium such as methanol or ethanol, at a temperature between $-10°$ C. and $+10°$ C., preferably at 0° C. during a period of 16 hours to 24 hours.

The amidine with the formula (I) can be obtained by treating the compound (VI) previously obtained, without any other purification, by an alcoholic solution of ammonia at a normality of 3N to 15N, at ambient temperature, and afterwards the mixture is heated to reflux for 1 to 3 hours.

The compounds with the formula (II) above, containing an asymmetric centre, can exist in the form of two isomers, (enantiomers). The invention also concerns each stereoisomer and its mixtures. The invention also includes addition salts with mineral or organic acids.

The present invention also concerns a preparation process for compounds with the formula (II) characterized in that the amino acid with the formula (IX) in its activated form (X):

in which R' represents an N-protector group and A represents the residue of a coupling reagent, is made to react with the amine with the formula (XI):

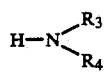

in which $R_3$ and $R_4$ are as described in formula (II), so as to form the compound with the formula (XII):

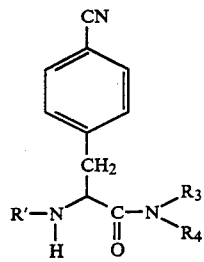

in which R', $R_3$ and $R_4$ have the previously given significances, which, by the action of compound $R_2X$ in which X is a halogen such as chlorine, bromine or iodine and $R_2$ is as defined in formula (II), leads to the compound with the formula (XIII):

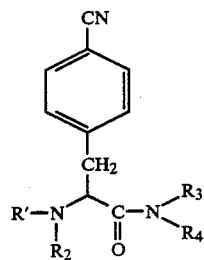

and by cleaving the protector group R', the compounds with the formula (II) are obtained.

The formation of the compound with the formula (IX) is obtained by fixation of the N-protector group R' on the p-cyanophenylalanine with the formula:

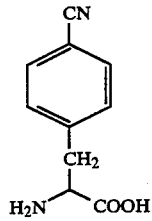

The N-protector group, represented by R', is one of the groups stable in an alkaline medium, used for the protection of amino groups of amino acids in the chemistry of peptides, for example the tertbutyloxycarbonyl group, preferably denoted hereafter Boc; the 2-(3,5-dimethoxyphenyl)-2-propyloxycarbonyl group denoted as Ddz; the 2-(biphenyl-4-yl)-2-propyloxycarbonyl group denoted as Bpoc; and the (2-nitrophenyl)sulphenyl group denoted as Nps.

In order to obtain the activated acid with the formula (X) in which A represents the residue of the coupling reagent, there are two cases to be considered.

(a) Preparation process with retention of the "R" or "S" configuration (stereospecific synthesis)

In order not to induce racemization at the asymmetric centre of the compound with the formula (XII) and to keep the initial configuration of the asymmetric centre of the acid with the formula (IX), it is necessary to use an activation of the acid (IX), using the conversion of the acid function into an activated ester (X) following the reactional scheme:

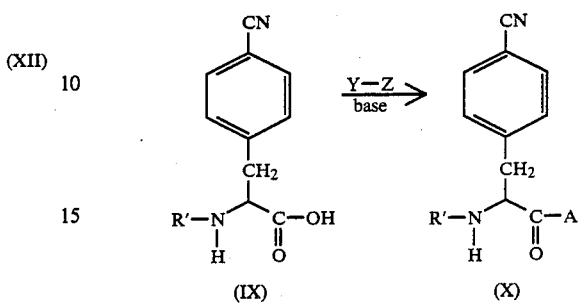

The coupling reagents Y-Z, not inducing racemization, which are preferably used, but non-limitative, are the following:

1-hydroxybenzotriazol (HOBT)

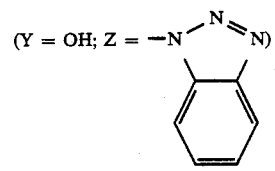

in the presence of N,N-dicyclohexylcarbodiimide (DCC) according to the operating method described by E. C. JORGENSEN et al. (J. Am. Chem. Soc. 1971, 93, 6318).

1-benzotriazolyl oxytris(dimethylamino)phosphonium hexafluorophosphate (BOP)

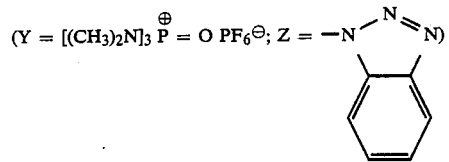

according to the operating method described by B. CASTRO et al. (Synthesis 1976, 751).

N,N-bis (2-oxo-3-oxazolidinyl)phosphorodiamide chloride

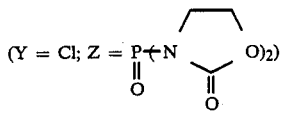

according to the operating method described by D. H. RICH et al. (J. Am. Chem. Soc. 1985, 107, 4342). The activation and coupling reaction take place in the presence of tertiary amines, preferably triethylamine, in an inert solvent such as dichloromethane, dimethylformamide or acetonitrile, at temperatures between 15° C. and 40° C.

(b) Preparation process without retention of the configuration (non-stereospecific synthesis)

The activation of the acid function of the compound (IX) can be carried out by conversion of the acid function into a mixed carbonic anhydride,

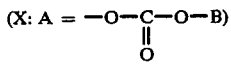

according to the reactional scheme:

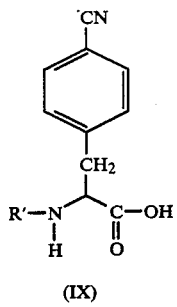
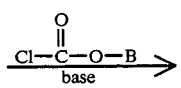

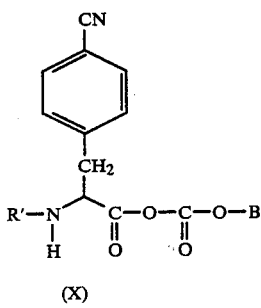

The reaction uses an alkyl chloroformate

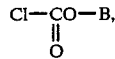

where B is a branched or unbranched lower alkyl, in the presence of a tertiary amine as a base. The alkyl chloroformate preferably used is ethyl chloroformate ($B=C_2H_5$) or isobutyl chloroformate ($B=CH_2-CH(CH_3)_2$).

The preferred tertiary amine is triethylamine. This condensation takes place preferably at temperatures between $-5°$ C. and $+10°$ C., in an inert solvent such as dichloromethane, chloroform or carbon tetrachloride.

The p-cyanophenylalanine used at the start has been prepared according to one of the methods used in the literature (G. WAGNER et al. Pharmazie 1981, 36 (9), 597).

The compound with the formula (X) is made to react with the amine with the formula (XI) in an inert solvent and in the presence of a tertiary amine.

The alkylation of compound (XII) uses one of the standard methods used in organic chemistry, by the action of the alkyl halogenide $R_2$-X, in which $R_2$ is as denoted above in the formula (II), and X is a halogen such as chlorine, bromine or preferably iodine.

This operation takes place in the presence of a strong base such as an alkaline hydride, preferably sodium hydride, in an inert solvent such as dimethylformamide or tetrahydrofuran, or an alkyllithium such as butyllithium or a lithium amide such as lithium diisopropylamide in an inert solvent such as hexane or tetrahydrofuran, at temperatures between 0° C. and 20° C.

The cleavage of the N-protector group R' of the compound with the formula (XIII) leads to Nα-substituted p-cyanophenylalaninamides with the formula (II). This cleavage takes place in an acid medium, preferably a hydrobromic acid-acetic acid mixture or in trifluoroacetic acid (R'=Boc, Ddz, Bpoc, Nps), in acetic acid, (R'=Boc, Nps), or in a saturated solution of hydrogen chloride gas in ethyl acetate (R'=Boc), at temperatures between 0° C. and 20° C.

EXAMPLE 1

Nα-(tertbutyloxycarbonyl) p-cyanophenylalanine

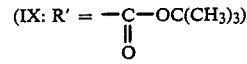

10 g (0.044 mole) of p-cyanophenylalanine hydrochloride is dissolved in 220 ml of dioxan and 88.2 ml (0.088 mole) of 1N aqueous sodium hydroxide. At ambient temperature and under inert atmosphere, 1.77 g (0.044 mole) of magnesium oxide is added in portions to the reactional medium, then 10.6 g (0.0484 mole) of ditertbutyl bicarbonate is added. The mixture is agitated at ambient temperature, for 20 hours. The crystals are filtered off and washed with water. The filtrate is evaporated and the residue is dissolved in water. The aqueous phase obtained is brought to pH=3 by addition of a saturated solution of potassium hydrogenosulphate. The aqueous phase is extracted with 2×400 ml of ethyl acetate; the organic extracts are dried on anhydrous sodium sulphate and evaporated to dryness. The crystals obtained are recrystallized from ethyl acetate or diisopropyl ether. White crystals, yield: 88%, m.p.=147° C.

EXAMPLE 2

1-[Nα-(tertbutyloxycarbonyl) p-cyanophenylalanyl]piperidine

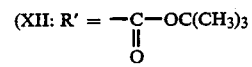

$NR_3R_4$=piperidino). Activation of the acid function of compound

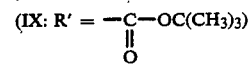

(example 1) in mixed carbonic anhydride

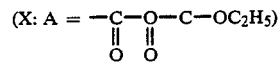

4.2 g (0.0416 mole) of triethylamine is added at 0° C., under inert atmosphere, to a suspension of 11 g (0.0378 mole) of Nα-(tertbutyloxycarbonyl)-p-cyanophenylalanine (example 1) in 125 ml of dichloromethane. To this mixture, which has become homogeneous, a solution of 4.3 g (0.0395 mole) of ethyl chloroformate in 10 ml of dichloromethane is added, drop by drop. After the final addition, the reactional mixture is left for 45 minutes, at 0° C., then, drop by drop, 3.4 g (0.0397 mole) of piperdine dissolved in 10 ml of dichloromethane is added. The reactional medium is allowed to return to ambient temperature and left for 15 hours at this temperature. The reactional medium is extracted with a saturated aqueous solution of sodium bicarbonate. The organic phase, after decanting, is dried on anhydrous sodium sulphate and evaporated to dryness. The oily residue gives white crystals, after trituration with diisopropyl ether. These crystals are recrystallized from diisopropyl ether. White crystals, yield: 81%, m.p.=132° C.

EXAMPLE 3

4-methyl-1-[Nα-(tertbutyloxycarbonyl) p-cyanophenylalanyl]piperidine

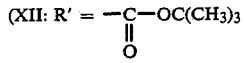

NR$_3$R$_4$=4-methylpiperidino). Activation by conversion of the acid function into an activated ester function, by use of a non-racemizing coupling reagent DCC/HOBT.

2.78 g (0.01 mole) of Nα-(tertbutyloxycarbonyl) p-cyanophenylalanine (example 1) is dissolved in 50 ml of dichloromethane. 1 g (0.01 mole) of 4-methylpiperidine, 1.35 g (0.01 mole) of 1-hydroxybenzotriazol (HOBT), and 1.1 g (0.01 mole) of triethylamine are added successively, under inert atmosphere and at ambient temperature. 2.06 g (0.01 mole) of N,N-dicyclohexylcarbodiimide (DDC) dissolved in 80 ml of dichloromethane is added to the reactional medium at ambient temperature, and the reactional medium is left for 15 hours at ambient temperature. The precipitate of dicyclohexylurea is filtered off and eliminated. The organic filtrate is washed with a saturated aqueous solution of sodium bicarbonate, and it is dried on anhydrous sodium sulphate. The evaporation leaves a residue which is triturated with diisopropyl ether. The white crystals obtained are recrystallized from ethyl acetate. White crystals, yield: 85%, m.p.=142° C. (ethyl acetate).

EXAMPLE 4

4-benzyl-1-[Nα-(tertbutyloxycarbonyl) p-cyanophenylalanyl]piperidine

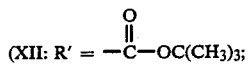

NR$_3$R$_4$=4-benzylpiperidino). Activation by conversion of the acid function into an activated ester function, by use of the non-racemizing coupling reagent BOP.

2.78 g (0.01 mole) of Nα-(tertbutyloxycarbonyl) p-cyanophenylalanine (example 1) is dissolved in 100 ml of acetonitrile and at ambient temperature, under an argon atmosphere, 4.43 g (0.01 mole) of 1-benzotriazolyl oxytris(dimethylamino)phosphonium hexafluorophosphate (BOP), 1.75 g (0.01 mole) of 4-benzylpiperidine and 1.1 g (0.01 mole) of triethylamine are added successively. The reactional medium is left for 16 hours at ambient temperature. The insoluble part is filtered off and removed. The filtrate is evaporated to dryness and taken up by dichloromethane. The organic phase is washed with a saturated aqueous solution of sodium bicarbonate, then dried on anhydrous sodium sulphate. Evaporation to dryness leaves a residue which is recrystallized from ethyl acetate. White crystals, yield: 78%, m.p.=131° C. (ethyl acetate).

EXAMPLE 5

1-(Nα-methyl p-cyanophenylalanyl)piperidine (II: R$_2$=CH$_3$; NR$_3$R$_4$=piperidino)

(a) Alkylation of 1-[Nα-(tertbutyloxycarbonyl) p-cyanophenylalanyl]piperidine.

13.1 g (0.0366 mole) of 1-[Nα-(tertbutyloxycarbonyl) p-cyanophenylalanyl]piperidine (example 2) dissolved in 150 ml of dimethylformamide is added, drop by drop, at ambient temperature, to a suspension of 1.84 g (0.038 mole) of sodium hydride, dispersed at 50% in oil, in 50 ml of dimethylformamide. The mixture is agitated for 45 minutes at ambient temperature and drop by drop 6.24 g (0.044 mole) of methyl iodide is added at this temperature. After the final addition, the mixture is left for one night at ambient temperature. The dimethylformamide is evaporated to dryness and the residue is taken up with water. The aqueous phase is extracted with ether. The ethereal extracts, after drying on anhydrous sodium sulphate and evaporation of the solvent, leave an oily residue, constituted by 1-[(Nα-methyl Nα-(tertbutyloxycarbonyl)) p-cyanophenylalanyl]piperidine (XIII: R$_1$=CH$_3$;

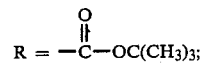

NR$_2$R$_3$=piperidino) which is used in the subsequent stage b) without any other purification.

(b) Deprotection

The oily residue obtained in the previous stage is dissolved in 150 ml of a saturated solution of hydrogen chloride gas in ethyl acetate and left for 2 hours at ambient temperature, then at 0° C. for one night. The crystals obtained are filtered off, washed with ether and recrystallized from isopropanol. White crystals, yield: 70%, m.p.=234° C. (isopropanol), hydrochloride. (global yield of stages (a)+(b)=70%)

EXAMPLE 6

1-(Nα-ethyl p-cyanophenylalanyl)piperidine (II: R$_2$=C$_2$H$_5$; NR$_3$R$_4$=piperidino)

Prepared according to the operating method described in example 5, by alkylation with ethyl iodide of 1-[Nα-(tertbutyloxycarbonyl) p-cyanophenylalanyl]piperidine (example 2), followed by deprotection by a saturated solution of hydrogen chloride gas in ethyl acetate. White crystals, global yield: 69%, m.p.=226° C. (isopropanol), hydrochloride.

EXAMPLE 7

4-methyl-1-(Nα-methyl p-cyanophenylalanyl)piperidine (II: R$_2$=CH$_3$; NR$_3$R$_4$=4-methylpiperidino).

Prepared according to the operating method described in example 5, by alkylation with methyl iodide of 4-methyl-1-[Nα-(tertbutyloxycarbonyl) p-cyanophenylalanyl]piperidine (example 3) followed by deprotection by a saturated solution of hydrogen chloride gas in ethyl acetate. White crystals, global yield: 80%, m.p.=214° C. (isopropanol), hydrochloride.

EXAMPLE 8

4-methyl-1-(Nα-ethyl p-cyanophenylalanyl)piperidine (II: $R_2=C_2H_5$; $NR_3R_4=$4-methylpiperidino).

Prepared according to the operating method described in example 5, by alkylation with ethyl iodide of 4-methyl-1-[Nα-(tertbutyloxycarbonyl) p-cyanophenylalanyl]piperidine (example 3), followed by deprotection by a saturated solution of hydrogen chloride gas in ethyl acetate. White crystals, global yield: 77%, m.p.=220° C. (isopropanol), hydrochloride.

EXAMPLE 9

4-benzyl-1-(Nα-methyl p-cyanophenylalanyl)piperidine (II: $R_2=CH_3$; $NR_3R_4=$4-benzylpiperidino).

Prepared according to the operating method described in example 5, by alkylation with methyl iodide of 4-benzyl-1-[Nα-(tertbutyloxycarbonyl) p-cyanophenylalanyl]piperidine (example 4), followed by deprotection by a saturated solution of hydrogen chloride gas in ethyl acetate. White crystals, global yield: 72%, m.p.=202° C. (isopropanol), hydrochloride.

EXAMPLE 10

1-[Nα(n-butyl) p-cyanophenylalanyl]piperidine (I: $R_2=$n-$C_4H_9$; $NR_3R_4=$piperidino).

(a) Alkylation 20 g (0.0558 mole) of 1-[Nα-(tertbutyloxycarbonyl) p-cyanophenylalanyl]piperidine (example 2) dissolved in 100 ml of dimethylformamide is added, drop by drop, to 2.8 g (0.0587 mole) of sodium hydride at 50% in oil, in suspension in 100 ml of dimethylformamide. After 45 minutes at ambient temperature, under argon atmosphere, 9.2 g (0.067 mole) of n-butyl bromide and 10 g of (0.067 mole) of sodium iodide are added. The mixture is left for one night at ambient temperature. The reactional medium is poured into water and evaporated to dryness. The residue is taken up with water and the aqueous solution is extracted with ether. The ethereal extracts, dried on anhydrous sodium sulphate, leave, after evaporation, an oily residue, constituted by 1-[Nα(n-butyl) Nα-(tertbutyloxycarbonyl) p-cyanophenylalanyl]piperidine

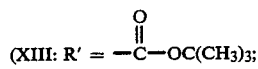

(XIII: $R' = -\overset{O}{\underset{\|}{C}}-OC(CH_3)_3$;

$R_2=$n-butyl; $NR_3R_4=$piperidino), which is used, without any other purification, in the subsequent deprotection stage.

(b) Deprotection

The process described in example 5b) is used. White crystals, global yield: 78%, m.p.=216° C. (isopropanol), hydrochloride.

EXAMPLE 11

1-(Nα-benzyl p-cyanophenylalanyl)piperidine (II: $R_2=CH_2$-$C_6H_5$; $NR_3R_4=$piperidino)

Prepared according to the operating method described in example 13, by alkylation with benzyl bromide of 1-[Nα-(tertbutyloxycarbonyl) p-cyanophenylalanyl]piperidine (example 2) followed by deprotection by a saturated solution of hydrogen chloride gas in ethyl acetate. White crystals, global yield: 64%, m.p.=212° C. (isopropanol), hydrochloride.

EXAMPLE 12

Ethyl N-beta-naphthylsulphonyl-glycinate (VIII: $A=C_2H_5$; $R_1=H$; $Ar=\beta$-naphthyl).

10 g (0.072 mole) of ethyl glycinate (VII: $A=C_2H_5$; $R_1=H$) is added in portions to a two-phase mixture of 50 ml of saturated aqueous solution of sodium bicarbonate and 50 ml of dichloromethane, under rapid mechanical agitation and at ambient temperature, and then 16.4 g (0.072 mole) of β-naphthylsulphonyl chloride is added. The reactional medium is left, under good agitation, at ambient temperature for 4 hours. The aqueous phase is decanted and removed. The organic phase is recovered and washed with a 2N aqueous solution of hydrochloric acid. The organic phase is dried on anhydrous sodium sulphate and evaporated to dryness. By trituration of the oily residue, obtained after evaporation, with diisopropyl ether, crystals are recovered which are recrystallized from ethyl acetate. White crystals, yield: 91%, m.p.=80° C. (ethyl acetate).

EXAMPLE 13

N-betanaphthylsulphonyl-glycine (III: $R_1=H$; $Ar=\beta$-naphthyl)

35 ml (0.07 mole) of 2N aqueous sodium hydroxide is added to a solution of 18.8 g (0.064 mole) of ethyl N-betanaphthylsulphonyl glycinate (example 12) in 200 ml of methanol, and the mixture is left at ambient temperature for 2 hours. The methanol is evaporated; the residue is taken up with water. The aqueous phase is extracted with ether and the ethereal extracts are removed. After neutralization of the aqueous phase with 35 ml of 2N hydrochloric acid, the crystals obtained are filtered, washed with water and dried. White crystals, yield: 73%, m.p.=157° C.

Examples 14 to 20 are carried out according to the same operating method as that described in example 12. They lead to compounds with the general formula (VIII: $Ar=\beta$-naphthyl; $A=CH_3$) and result from the N-sulphonylation of methyl esters of amino acids (VII: $A=CH_3$) with "R" or "S" configuration, by β-naphthylsulphonyl chloride. They are grouped together in the following table:

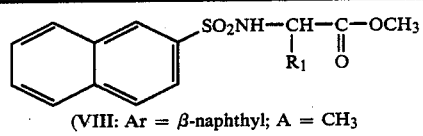

(VIII: $Ar = \beta$-naphthyl; $A = CH_3$

| Example | $R_1$ | Configuration of aminoacid | Yield | F° (isopropanol) |
|---|---|---|---|---|
| 14 | $CH_3$ | R | 72% | 98° C. |
| 15 | $CH_3$ | S | 64% | 97° C. |
| 16 | $CH(CH_3)_2$ | S | 67% | 106° C. |
| 17 | $CH_2OH$ | S | 40% | 150° C. |
| 18 | $CH_2$—$C_6H_5$ | R | 64% | 160° C. |
| 19 | $C_6H_5$ | R | 84% | 158° C. |
| 20 | $CH(CH_3)OH$ | S | 50% | 142° C. |

Examples 21 to 27 are carried out according to the same operating method as that described in example 13. They lead to acids with the general formula (III: $Ar=\beta$-naphthyl) and result from the saponification of esters with the general formula (VIII: $Ar=\beta$-naphthyl, $A=CH_3$). They are grouped together in the following table:

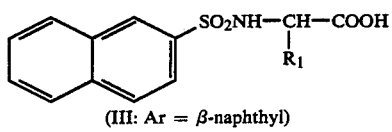

(III: Ar = β-naphthyl)

| Example | R₁ | Configuration of aminoacid | Yield | F° C. |
|---|---|---|---|---|
| 21 | CH₃ | R | 89% | 116° C. |
| 22 | CH₃ | S | 90% | 124° C. |
| 23 | CH(CH₃)₂ | S | 76% | 166° C. |
| 24 | CH₂OH | S | 76% | 210° C. |
| 25 | CH₂—C₆H₅ | R | 90% | 60° C. |
| 26 | C₆H₅ | R | 93% | 160° C. |
| 27 | CH(CH₃)OH | R | 66% | 194° C. |

EXAMPLE 28

Ethyl N-(8-quinolinylsulphonyl)-glycinate (VIII: Ar=quinolinyl; A=C₂H₅; R₁=H)
Prepared according to the operating method described in example 12, by sulphonylation of ethyl glycinate (VII: A=C₂H₅; R₁=H) by (8-quinolinyl)sulphonyl chloride. White crystals, m.p.=112° C. (ethyl acetate); yield: 91%.

EXAMPLE 29

N-(8-quinolinylsulphonyl)-glycine (III: Ar=8-quinolinyl; R₁=H)
Prepared according to the operating method described in example 13. White crystals, yield: 99%; m.p.=129° C.

EXAMPLE 30

1-[Nα-methyl Nα-(N'-betanaphthylsulphonylglycyl) p-cyanophenylalanyl]piperidine (V: Ar=β-naphthyl; R₁=H; R₂=C₂H₅; NR₃R₄=piperidino)

2.1 g (0.078 mole) of N(betanaphthylsulphonyl)-glycine (example 2) in 20 ml of thionyl chloride is brought to reflux for one hour, under inert atmosphere. The reactional medium is evaporated to dryness and the oily residue is dissolved in 50 ml of dichloromethane. Acid chloride which has been dissolved in dichloromethane is added drop by drop under inert atmosphere, to a solution of 1 g (0.0031 mole) of 1-(Nα-methyl p-cyanophenylalanyl)piperidine hydrochloride (II: R₂=CH₃; NR₃R₄=piperidino) and 1.14 g (0.0112 mole) of triethylamine, in 20 ml of dichloromethane, which has previously been cooled to between 0° C. and 5° C. The reactional medium is left at ambient temperature for 20 hours. The insoluble salts are filtered off and the filtrate is evaporated to dryness. The residue is taken up by 1N hydrochloric acid and the aqueous acid phase obtained is extracted by dichloromethane. The organic extracts are dried on anhydrous sodium sulphate and evaporated to dryness. The residue obtained after evaporation is purified by chromatography on a silica column (elution: toluene-ethyl acetate 1:1). White crystals are obtained. White crystals, yield: 69%, m.p. 130° C. (isopropanol)

Examples 31 to 33 are carried out according to the same operating method as that described in example 30. They lead to nitriles with the formula (V: Ar=β-naphthyl, R₁=H) and result from the coupling of synthons with the general formula (II) with acids with the formula (III: Ar=β-naphthyl; R₁=H), previously activated into acid halogenides, by treatment with, preferably, thionyl chloride. They are grouped together in the following table:

| Example | R₂ | NR₃R₄ | Yield | F° C. solvent recrystallization |
|---|---|---|---|---|
| 31 | CH₂—C₆H₅ | piperidino | 44% | oil |
| 32 | C₂H₅ | 4-methylpiperidino | 49% | 74° C. diisopropyl ether |
| 33 | n-C₄H₉ | piperidino | 40% | 142° C. (isopropanol) |

EXAMPLE 34

1-[Nα-ethyl Nα-(N'-betanaphthylsulphonylglycyl) p-cyanophenylalanyl]piperidine (V: Ar=β-naphthyl; R₁=H; R₂=C₂H₅; NR₃R₄=piperidino)

2.6 g (0.0253 mole) of triethylamine is added to a suspension of 6.1 g (0.023 mole) of N(betanaphthylsulphonyl)glycine (example 13) in 80 ml of dichloromethane, maintained between 0° C. and 5° C., then drop by drop 3.4 g (0.025 mole) of isobutyl chloroformate is added, and the mixture is left for one hour at this temperature. Then 7.5 g (0.024 mole) of 1-(Nα-ethyl p-cyanophenylalanyl)piperidine (II: R₂=C₂H₅; NR₃R₄=piperidino) is added, dissolved in 50 ml of dichloromethane, and the reactional medium is left at ambient temperature for 20 hours. It is evaporated to dryness, and the residue is taken up with water. The aqueous phase is extracted by dichloromethane. The organic extracts are dried on anhydrous sodium sulphate and evaporated to dryness. The oily residue is purified by chromatography on a silica column (elution: toluene-ethyl acetate 1:1). White crystals, yield: 74.5%; m.p.=82° C. (ethyl acetate)

EXAMPLE 35

1-[Nα-methyl Nα-(N'-betanaphthylsulphonyl-(S)-alanyl) p-cyanophenylalanyl]piperidine (V: Ar=β-naphthyl; R₁=CH₃; R₂=CH₃; NR₃R₄=piperidino).

(a) Coupling not inducing racemization using coupling reagent 1-hydroxybenzotriazol (HOBT)/N,N-dicyclohexylcarbodiimide (DCC).

15.1 g (0.0425 mole) of Nα-(betanaphthylsulphonyl)-(S)-alanine (III=example 22), 4.3 g (0.0425 mole) of triethylamine and 6.5 g (0.0425 mole) of 1-hydroxybenzotriazol (HOBT) are added successively to a suspension of 13 g (0.0425 mole) of 1-(Nα-methyl p-cyanophenylalanyl)piperidine hydrochloride (II: $R_2=CH_3$; $NR_3R_4$=piperidino) in 200 ml of dichloromethane. The reactional medium is cooled to between 0° C. and 5° C. and drop by drop 8.8 g (0.0425 mole) of N,N-dicyclohexylcarbodiimide (DCC) dissolved in 50 ml of dichloromethane is added. The reactional medium is left, under good agitation, at ambient temperature, for 17 hours. The precipitate of dicyclohexylurea is filtered off and the organic filtrate is washed with a saturated aqueous solution of sodium bicarbonate. The organic phase, dried on anhydrous sodium sulphate, is evaporated to dryness. The evaporation of the solvent leaves a residue which is triturated with ethyl acetate. The white crystals are filtered and washed with diisopropyl ether. White crystals, yield: 62%; m.p.=110° C. (ethyl acetate).

(b) Coupling not inducing racemization, using coupling reagent 1-benzotriasolyl oxytris(dimethylamino)-phosphonium hexafluorophosphate (BOP).

11.9 g (0.027 mole) of 1-benzotriazolyl oxytris(dimethylamino)phosphonium hexafluorophosphate (BOP), 8.3 g (0.027 mole) of 1-(Nα-methyl p-cyanophenylalanyl)piperidine hydrochloride (II: $R_2=CH_3$; $NR_3R_4$=piperidino) and 5.5 g (0.054 mole) of triethylamine are added successively to a solution of 7.5 g (0.027 mole) of Nα-(betanaphthylsulphonyl)-(S)-alanine (III: example 22) in 300 ml of acetonitrile. The reactional medium is left under inert atmosphere, under good agitation, at ambient temperature, for 20 hours. The reactional medium is diluted with ethyl acetate and washed successively with a saturated aqueous solution of sodium chloride, with a 2N solution of hydrochloric acid, with water, and with a saturated aqueous solution of sodium bicarbonate, then with water. The organic phase is dried on anhydrous sodium sulphate and evaporated to dryness. The residue is purified by chromatography on a silica column (elution: toluene-ethyl acetate 1:1). White crystals are recovered which are dried. White crystals, yield: 42%; m.p.=110° C.

Examples 36 to 41 are carried out according to the same operating method as that described in example 35a). They lead to nitriles with the formula (V) and result from the coupling of synthons with the general formula (II) with acids with the general formula (III) previously activated by the conversion of the acid function into an activated ester function, using the non-racemizing coupling reagent DCC/HOBT. They are grouped together in the following table:

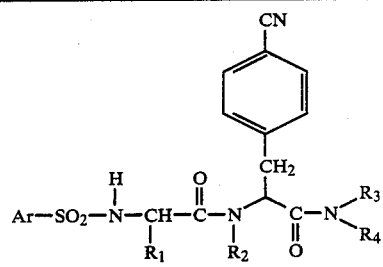

| Example | Ar | $R_1$ | $R_2$ | $NR_3R_4$ | Yield | F° C. |
|---|---|---|---|---|---|---|
| 36 | naphthyl | H | $CH_3$ | N-piperidinyl-$CH_3$ | 92% | 143° C. |
| 37 | methylquinolinyl | H | $CH_3$ | N-piperidinyl-$CH_3$ | 37% | 202° C. |
| 38 | quinolinyl | H | $CH_3$ | N-piperidinyl-$CH_3$ | 51% | 102° C. |
| 39 | quinolinyl | H | $CH_3$ | piperidinyl | 56% | 60° C. |

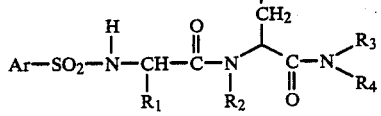

| Example | Ar | $R_1$ | $R_2$ | $NR_3R_4$ | Yield | F° C. |
|---|---|---|---|---|---|---|
| 40 | (quinolinyl) | H | $CH_3$ | piperidino | 35% | 212° C. |
| 41 | (o-COOCH₃-phenyl) | H | $CH_3$ | piperidino | 88% | 100° C. [pasty] |

Examples 42 to 45 use the same operating method as that described in example 35b). They lead to nitriles (V: Ar=β-naphthyl) and result from the coupling of synthons with the general formula (II) with acids with the general formula (III), previously activated by conversion of the acid function into an activated ester function, using the non-racemizing coupling reagent BOP. They are grouped together in the following table:

EXAMPLE 46

1-[Nα-methyl Nα-(N'-betanaphthylsulphonylglycyl) p-amidinophenylalanyl]piperidine (I: Ar=β-naphthyl; $R_1$=H; $R_2$=$CH_3$; $NR_4$=piperidino).

Derivative No. 1

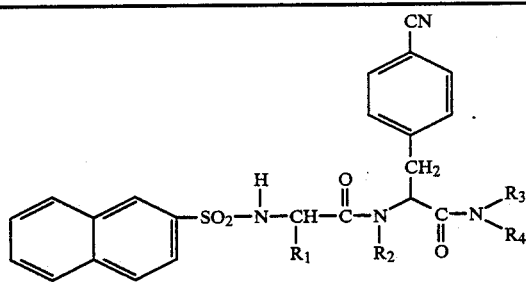

| Example | (configuration of aminoacid) | $R_2$ | $NR_3R_4$ | Yield | F° C. |
|---|---|---|---|---|---|
| 42 | H | $CH_3$ | N-piperidinyl-CH₂-phenyl | 40% | 82° C. |
| 43 | $CH(CH_3)_2$(S) | $CH_3$ | piperidino | 40% | 228° C. |
| 44 | $CH_2OH$(S) | $CH_3$ | piperidino | 67% | 102° C. |
| 45 | $CH(CH_3)OH$(S) | $CH_3$ | piperidino | 66% | 98° C. |

(a) Formation of the imidoester 80 ml of methanol is saturated at 0° C., under under inert atmosphere with hydrogen chloride gas, and 5.3 g (0.01 mole) of 1-[Nα-methyl Nα(N'-betanaphthylsulphonylglycyl) p-cyanophenylalanyl]piperidine (V: example 30) is added all at once to this solution; the mixture is left for 20 hours at 0° C. The methanol is evaporated to dryness, without heating, and a white resin is obtained, constituted by the hydrochloride of the imidoester with the general formula (VI: Ar=β-naphtyl; $R_1$=H; $R_2$=CH$_3$; NR$_3$R$_4$=piperidino; X=CH$_3$) which is used without any other purification in the subsequent stage.

(b) Formation of the amidine 80 ml of methanol is saturated at 0° C. to 5° C., under inert atmosphere, with ammonia gas, and to this ammonia-methanol solution the white resin obtained in the previous stage (example 46a) is added, after dissolving in 20 ml of methanol. The reactional mixture is brought to reflux, under inert atmosphere, for 3 hours. It is evaporated to dryness and the residue is taken up by 1N hydrochloric acid, in excess. The aqueous acid phase is extracted by dichloromethane. The organic phase is dried on anhydrous sodium sulphate and evaporated to dryness. The semi-crystalline residue obtained is dissolved in water. The aqueous solution obtained is extracted by ethyl acetate, and the organic extracts are isolated. The organic phase is lyophilized and the semi-crystalline residue is triturated with ethyl ether. The white crystals are filtered, washed with ether and dried. The final product is in the form of hydrated hydrochloride. White crystals, yield: 70; m.p.=170° C. (hydrochloride, dihydrate).

For derivatives 2 to 15, the same operating methods are used as those described in example 46. They lead to Nα-arylsulphonylaminoacyl p-amidinophenylalaninamides with the general formula (I) and result from the conversion of nitriles with the general formula (V) into amidines with the general formula (I) by the intermediary of imidoesters with the general formula (VI). They are grouped together in the following table:

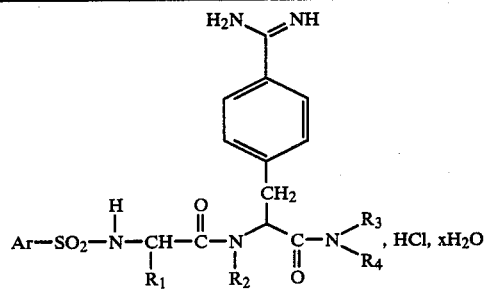

| Deriv. | Ar | (configuration of aminoacid) | $R_2$ | NR$_3$R$_4$ | x | Yield | F° |
|---|---|---|---|---|---|---|---|
| 2 | β-naphthyl | H | CH$_3$ | 4-methylpiperidino | 1.5 | 64% | 160° |
| 3 | β-naphthyl | H | C$_2$H$_5$ | piperidino | 1.5 | 56% | 168° |
| 4 | β-naphthyl | H | CH$_2$—C$_6$H$_5$ | piperidino | 2 | 64% | 170° |
| 5 | β-naphthyl | H | C$_2$H$_5$ | 4-methylpiperidino | 1 | 50% | 164° |
| 6 | β-naphthyl | H | n-C$_4$H$_9$ | piperidino | 1.5 | 54% | 154° |
| 7 | β-naphthyl | CH$_3$(S) | CH$_3$ | piperidino | 1.5 | 71% | 162° |

-continued

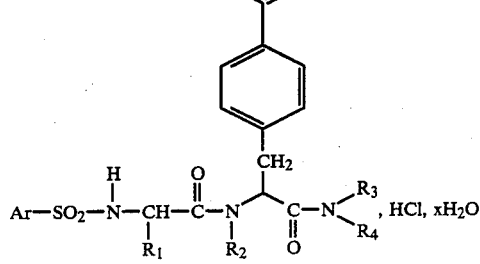

| Deriv. | Ar | (configuration of aminoacid) | R₂ | NR₃R₄ | x | Yield | F° |
|---|---|---|---|---|---|---|---|
| 8 | 2-naphthyl | H | CH₃ | 4-benzylpiperidin-1-yl | 1.5 | 57% | 160° |
| 9 | 3-methylquinolin-8-yl | H | CH₃ | 4-methylpiperidin-1-yl | 2 | 46% | 196° |
| 10 | quinolin-8-yl | H | CH₃ | 4-methylpiperidin-1-yl | 3 | 76% | 185° |
| 11 | quinolin-8-yl | H | CH₃ | piperidin-1-yl | 4.5 | 51% | 160° |
| 12 | 2-naphthyl | CH(CH₃)₂(S) | CH₃ | piperidin-1-yl | 3 | 48% | 175° |
| 13 | 2-naphthyl | CH(CH₃)OH (S) | CH₃ | piperidin-1-yl | 2 | 76% | 169° |
| 14 | 2-naphthyl | CH₂OH (S) | CH₃ | piperidin-1-yl | 1.5 | 72% | 170° |
| 15 | 2-(COOCH₃)phenyl | H | CH₃ | piperidin-1-yl | 1.5 | 28% | 158° |

The results of the toxicological and pharmacological studies which are set out below give evidence of the useful properties of the compounds of the invention.

These latter are endowed with a very good inhibiting activity for thrombin and possess in addition remarkable antithrombotic properties in vivo which the compounds with the formulae (A) and (B) and the compound (C) do not show.

Compared to heparin they have a much better duration of action without inducing an increase in the bleeding time.

The subject of the invention is therefore also a medicament presenting in particular antithrombotic properties, characterized in that it contains, as active principle, a compound with the formula (I) or an addition salt with a therapeutically acceptable mineral or organic acid.

Toxicological Study

The compounds of the invention have the benefit of a good tolerance and a weak toxicity. Tests carried out on various types of animal on the acute, subchronic and chronic toxicity did not give evidence of any local or general reaction, disturbance or anomaly in the biochemical, macroscopic and microscopic examinations carried out throughout the tests.

Pharmacological Study

In this study, the compounds of the invention have been compared with heparin and with 1-[Nα-(N-betanaphthylsulphonylglycyl) p-amidinophenylalanyl]-piperidine, a compound with a similar structure described as a powerful thrombin inhibitor (J.HAUPTMANN et al. Thromb, Res, 39, 771–775, 1983) and which will be called derivative C.

(1) Determination of the specificity vis-à-vis thrombin.

A number of serin-proteases (factors XIIa, IXa, VIIa, Xa, thrombin plasmin) exist in plasma and take part in the coagulation mechanism. In order not to induce too significant disturbances in the "cascade of coagulation" and involve risks of hemorrhage, it is advisable to ascertain that the compounds chosen possess a specific action on thrombin. On the other hand, in order to obtain a good activity by oral route, it is also necessary to have a good specificity vis-à-vis trypsin, a serin-protease of the digestive tract.

Therefore the inhibiting constants of bovine thrombin (Sigma 2000 MH/mg) in vitro have been determined by Dixon's method (Biochem. J., 1953, 55, 170–171), on hydrolysis of substrate 2238 (Kabi Vitrum) at pH 8 and at 25° C., and those of bovine trypsin (Sigma type III-S) in the same conditions.

The results are set out in the following table:

| Derivative | $K_I$ Thrombin | $K_I$ Trypsin |
|---|---|---|
| 1 | $0.27 \cdot 10^{-8}$ M | $0.10 \cdot 10^{-6}$ M |
| 11 | $1.52 \cdot 10^{-7}$ M | $1.2 \cdot 10^{-6}$ M |
| 2 | $2.15 \cdot 10^{-8}$ M | $0.12 \cdot 10^{-6}$ M |
| C | $10^{-8}$ M | $0.75 \cdot 10^{-6}$ M |

(2) Thrombin time.

The coagulation time of citrated plasma in the presence of thrombin is measured ex vivo in the rat according to the technique of BIGGS R. M. (Human blood coagulation, haemostasis and thrombosis; Oxford, Blackwell Scientific Publications, 1972).

Samples are taken one hour after sub-cutaneous administration of the compound under test, by puncture of the abdominal aorta. The blood is collected on sodium citrate at 3.8% (1 volume for 9 volumes of blood). The plasma is obtained by centrifuging at 2600 g for 10 minutes. 0.2 ml of a solution of thrombin (20 U/ml) is added to the plasma. The coagulation time is recorded. The results are set out in the following table:

| | Dose mg/kg | Route | Results [Time in seconds] | % Prolongaton | p |
|---|---|---|---|---|---|
| Control | 10 | S.C | 6 ± 0 | | |
| Heparin | | S.C | 20 ± 4 | 233 | 0.001 |
| Control | 10 | S.C | 7 ± 0 | | |
| Deriv. C | | S.C | 9 ± 0 | 29 | 0.001 |
| Control | 10 | S.C | 7 ± 0 | | |
| Deriv. no 1 | | S.C | 114 ± 16 | 1529 | 0.001 |
| Control | 10 | S.C | 6 ± 0 | 200 | 0.001 |
| Deriv. no 3 | | S.C | 18 ± 2 | | |
| Control | 10 | S.C | 8 ± 0 | 750 | 0.001 |
| Deriv. no 11 | | S.C | 68 ± 6 | | |
| Control | 10 | S.C | 9 ± 0 | 33 | 0.001 |
| Deriv. no 5 | | S.C | 12 ± 1 | | |
| Control | 10 | S.C | 8 ± 0 | 255 | 0.05 |
| Deriv. no 13 | | S.C | 28 ± 5 | | |
| Control | 10 | S.C | 7 ± 0 | 1370 | 0.01 |
| Deriv. no 14 | | S.C | 105 ± 17 | | |

(3) Venous thrombosis with the spiral.

The tests were carried out according to an adaptation of the method of T. KUMADA et al. (Thromb. Res., 18, 189–203, 1980).

A metallic spiral (a re-cut dentist's paste rammer) is inserted into the lower vena cava of the anaesthetized rat. One hour earlier the animals received the compound under test by sub-cutaneous route. Five hours later, the spiral is removed with the thrombus which it retains, then dried by repeated dabbing with filter paper and weighed. The spiral is then freed of the thrombus, dried and weighed again. The weight difference gives the weight of the thrombus.

The results are set out in the following table:

| Product | Dose mg/kg | Weight of thrombus in mg | Variation | p |
|---|---|---|---|---|
| control | | 4.47 ± 0.51 | | |
| heparin | 5 | 2.91 ± 0.53 | −35% | 0.05 |
| heparin | 10 | 1.62 ± 0.34 | −64% | 0.001 |
| heparin | 20 | 0.26 ± 0.04 | −94% | 0.001 |
| control | | 4.77 ± 0.47 | | |
| derivative C | 20 | 3.99 ± 0.45 | −16% | n.s. |
| derivative C | 50 | 3.63 ± 0.37 | −24% | n.s. |
| derivative C | 100 | 3.08 ± 0.28 | −35% | 0.01 |
| control | | 3.51 ± 0.53 | | |
| derivative No. 1 | 5 | 2.43 ± 0.17 | −31% | n.s. |
| derivative No. 1 | 10 | 2.01 ± 0.20 | −43% | 0.05 |
| derivative No. 1 | 20 | 1.34 ± 0.12 | −62% | 0.01 |
| derivative No. 1 | 50 | 0.87 ± 0.07 | −75% | 0.001 |
| control | | 4.53 ± 0.55 | | |
| derivative No. 3 | 10 | 2.46 ± 0.16 | −46% | 0.01 |
| control | | 3.85 ± 0.21 | | |
| derivative No. 13 | 10 | 1.36 ± 0.14 | −65% | 0.001 |
| control | | 4.10 ± 0.43 | | |
| derivative No. 11 | 5 | 3.13 ± 0.38 | −24% | n.s. |
| derivative No. 11 | 10 | 2.02 ± 0.19 | −51% | 0.001 |
| derivative No. 11 | 20 | 1.85 ± 0.13 | −55% | 0.001 |
| control | | 4.11 ± 0.33 | | |
| derivative No. 5 | 10 | 3.25 ± 0.24 | −21% | 0.05 |
| control | | 3.85 ± 0.21 | | |
| derivative No. 14 | 10 | 0.79 ± 0.19 | −80% | 0.001 |

Kinetic study of venous thrombosis with the spiral

The comparative study of the kinetics effecting heparin and the derivative No. 1 was carried out.

The derivatives under test are administered by sub-cutaneous route 15 minutes, 1 hour, 2 hours, 4 hours, 6 hours, 16 hours and 48 hours before the positioning of the spiral, which is removed 5 hours later.

The weight of the thrombus is determined.

The results are set out in the following table.

| Product | Dose mg/kg | Route | Time | Weight of thrombus in mg | Variation | p |
|---|---|---|---|---|---|---|
| Control | | s.c. | | 4.21 ± 0.34 | | |
| Heparin | 10 | s.c. | −15 mn | 4.21 ± 0.34 | −58% | 0.001 |
| Heparin | 10 | s.c. | −1 H | 0.82 ± 0.22 | −80% | 0.001 |
| Heparin | 10 | s.c. | −4 H | 1.18 ± 0.12 | −72% | 0.001 |
| Heparin | 10 | s.c. | −6 H | 2.67 ± 0.35 | −36% | 0.001 |
| Control | | s.c. | | 4.55 ± 0.55 | | |
| Heparin | 10 | s.c. | −2 H | 0.55 ± 0.09 | −88% | 0.001 |
| Control | | s.c. | | 4.19 ± 0.37 | | |
| Heparin | 5 | s.c. | −15 mn | 3.70 ± 0.29 | −12% | n.s. |
| Heparin | 5 | s.c. | −1 H | 1.73 ± 0.26 | −59% | 0.001 |
| Heparin | 5 | s.c. | −4 H | 3.10 ± 0.43 | −26% | n.s. |
| Heparin | 5 | s.c. | −6 H | 3.15 ± 0.28 | −25% | n.s. |
| Control | | s.c. | | 4.35 ± 0.43 | | |
| Heparin | 5 | s.c. | −2 H | 3.04 ± 0.25 | −30% | 0.05 |
| Control | | s.c. | | 3.37 ± 0.33 | | |
| Deriv. n° 1 | 20 | s.c. | −15 mn | 1.99 ± 0.24 | −41% | 0.01 |
| Deriv. n° 1 | 20 | s.c. | −1 H | 1.67 ± 0.15 | −50% | 0.001 |
| Control | | s.c. | | 3.91 ± 0.42 | | |
| Deriv. n° 1 | 20 | s.c. | −2 H | 1.82 ± 0.10 | −53% | 0.001 |
| Control | | s.c. | | 3.95 ± 0.32 | | |
| Deriv. n° 1 | 20 | s.c. | −4 H | 1.40 ± 0.13 | −63% | 0.001 |
| Deriv. n° 1 | 20 | s.c. | −6 H | 1.40 ± 0.13 | −43% | 0.001 |
| Control | | s.c. | | 3.52 ± 0.44 | | |
| Deriv. n° 1 | 20 | s.c. | −16 H | 2.64 ± 0.38 | −25% | n.s. |
| Control | | s.c. | | 3.20 ± 0.23 | | |
| Deriv. n° 1 | 50 | s.c. | −15 mn | 1.31 ± 0.08 | −59% | 0.001 |
| Deriv. n° 1 | 50 | s.c. | −1 H | 0.92 ± 0.08 | −71% | 0.001 |
| Deriv. n° 1 | 50 | s.c. | −2 H | 1.01 ± 0.08 | −68% | 0.001 |
| Deriv. n° 1 | 50 | s.c. | −4 H | 0.82 ± 0.07 | −74% | 0.001 |
| Control | | s.c. | | 3.77 ± 0.36 | | |
| Deriv. n° 1 | 50 | s.c. | −6 H | 1.21 ± 0.16 | −68% | 0.001 |
| Control | | s.c. | | 3.70 ± 0.24 | | |
| Deriv. n° 1 | 50 | s.c. | −16 H | 1.69 ± 0.26 | −54% | 000.1 |
| Control | | s.c. | | 2.98 ± 0.39 | | |
| Deriv. n° 1 | 50 | s.c. | −48 H | 2.49 ± 0.30 | −16% | n.s. |

(4) Bleeding time.

This study was carried out according to an adaptation of the technique of L. STELLA et al. (Thromb. Res.; 1975, 7, 709–716).

After anaesthetizing the rat with pentobarbital, the tail is amputated 5 mm from the end and the blood from the wound is dabbed carefully every 15 seconds with a filter paper until haemostasis occurs. The latter is reached when no spot of blood appears for one minute. The products under test are administered by subcutaneous route, one hour before the cutting of the tail. The results are set out in the following table:

| Product | Dose mg/kg | Duration in seconds | Extremes | p |
|---|---|---|---|---|
| Control | | 360 | 330–480 | |
| Heparin | 5 | 465 | 330–540 | n.s. |
| Heparin | 10 | 3600 | 525−>3600 | 0.01 |
| Heparin | 20 | 3600 | 690−>3600 | 0.01 |
| Control | | 540 | 405–675 | |
| Deriv. C | 10 | 375 | 360–510 | n.s. |
| Deriv. C | 20 | 750 | 420–960 | n.s. |
| Deriv. C | 50 | 600 | 435–615 | n.s. |
| Control | | 405 | 390–510 | |
| Deriv. n° 1 | 10 | 450 | 420–525 | n.s. |
| Deriv. n° 1 | 20 | 480 | 420–3600 | n.s. |
| Deriv. n° 1 | 50 | 465 | 360−>3600 | n.s. |
| Control | | 480 | 405–840 | |
| Deriv. n° 1 | 100 | 795 | 600–1140 | n.s. |
| Deriv. n° 1 | 100 | 960 | 600–1020 | 0.05 |
| Control | | 525 | 460–600 | |
| Deriv. n° 11 | 5 | 615 | 540–780 | n.s. |
| Deriv. n° 11 | 10 | 690 | 495–750 | n.s. |
| Deriv. n° 11 | 20 | 585 | 495–855 | n.s. |
| Deriv. n° 11 | 50 | 540 | 450–660 | n.s. |

Kinetic study of bleeding time

The comparative study of the kinetics effecting heparin and the derivative No. 1 was carried out.

The derivatives under test are administered by subcutaneous route 15 minutes, 1 hour, 2 hour, 4 hours and 6 hours before anaesthesis and cutting the tail.

The results are set out in the following table.

| Product | Dose mg/kg | Time | Duration in seconds | Extremes | p |
|---|---|---|---|---|---|
| Control | | | 330 | 240–405 | |
| Heparin | 10 | −15 mn | 465 | 315–510 | n.s. |
| Heparin | 10 | −1 H | >3600 | 405−>3600 | 0.05 |
| Heparin | 10 | −4 H | >3600 | 600−>3600 | 0.01 |
| Heparin | 10 | −6 H | 390 | 315–495 | n.s. |
| Control | | | 412 | 360–540 | |
| Deri. no 1 | 10 | −15 mn | 465 | 300–690 | n.s. |
| Deri. no 1 | 10 | −1 H | 555 | 390–570 | n.s. |
| Deri. no 1 | 10 | −4 H | 480 | 465–540 | n.s. |
| Deri. no 1 | 10 | −6 H | 450 | 390–870 | n.s. |
| Control | | | 465 | 360–795 | |
| Deri. no 1 | 20 | −15 mn | 540 | 390–720 | n.s. |
| Deri. no 1 | 20 | −1 H | 480 | 435–630 | n.s. |
| Deri. no 1 | 20 | −2 H | 540 | 405–520 | n.s. |
| Deri. no 1 | 20 | −4 H | 585 | 405–1800 | n.s. |
| Deri. no 1 | 20 | −6 H | 450 | 300–840 | n.s. |

These studies which have just been carried out have given evidence of the remarkable effects of the derivatives of the invention.

antithrombotic power=determination of thrombin time and the test with the spiral have shown that the compounds of the invention produced a much better activity than derivative C and that they possessed the advantage over heparin of a much more lasting action; in fact, if in the first few hours the effects of the heparin and of the derivative No. 1 are superposable, after 6 hours, the heparin shows a noticeable falling off whereas derivative No. 1 still produces a decrease in the weight of the thrombus of 68% and 48 hours later of 16%.

It can be concluded from this that, with equivalent anti-thrombotic activity, the derivatives of the invention bring a notable security in the greater time, with 16 hours, by comparison with heparin (3–4 hours).

bleeding time=the kinetic study has clearly shown the risk of hemorrhage caused by heparin. The derivative of the invention, while only slightly prolonging the bleeding time, allows a safety margin much greater than that of heparin.

The subject of the invention is also a medicament presenting in particular antithrombotic activities characterized in that it contains as active principle a derivative with the formula (I) or an addition salt with a pharmaceutically acceptable mineral or organic acid.

The medicament of the invention can be presented for oral administration in the form of tablets, sugar-coated tablets, capsules, drops, syrup or granules. It can also be presented for rectal administration in the form of suppositories and for parenteral administration in the form of an injectable solution.

Each unit dose advantageously contains from 0.005 g to 0.500 g of active principle as a function of the age of the invalid and of the seriousness of the affection treated. By way of non-limitative examples, there are given below some pharmaceutical formulations of the medicament of the invention.

| | |
|---|---|
| (1) Sugar-coated tablets | |
| Derivative No. 1 | 0.050 g |
| Excipient | Lactose, polyvinylpyrrolidone, magnesium stearate, talc, calcium carbonate, silica, titanium oxide, gum arabic, white wax, carnauba wax. |
| (2) Tablets | |
| Derivative No. 2 | 0.025 g |
| Excipient | Lactose, microcrystalline cellulose, talc, magnesium stearate. |
| (3) Capsules | |
| Derivative No. 3 | 0.100 g |
| Excipient | Talc, wheat starch, magnesium stearate. |
| (4) Suppositories | |
| Derivative No. 5 | 0.050 g |
| Excipient | semi-synthetic glycerides. |
| (5) Injectable solution | |
| Derivative No. 11 | 0.025 g |
| Excipient | Isotonic solvent, q.s. for 3 ml. |

For its anticoagulant and antithrombotic properties, without secondary effects due to the risk of hemorrhage, the medicament of the invention is usefully administered in the prevention and treatment of thromboembolic disease.

We claim:

1. Compounds with the formula:

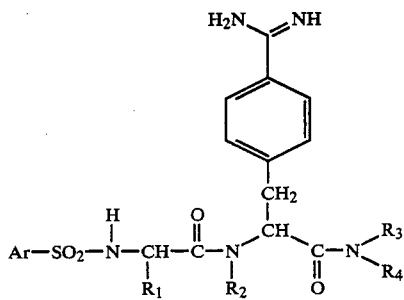

in which:
$R_1$ represents hydrogen, a $C_{1-6}$ alkyl group, $C_{1-6}$ hydroxyalkyl group, a benzyl group, a phenyl group or a 4-hydroxyphenyl group;
$R_2$ represents a $C_{1-6}$ alkyl, $C_{1-6}$ alkenyl, or $C_{1-6}$ alkynyl group, or a benzyl group, or a $C_{1-6}$ alkoxycarbonylalkyl, $C_{1-6}$ carboxyalkyl or $C_{1-6}$ hydroxyalkyl group;
$R_3$ and $R_4$, identical or different, each represents a $C_{1-6}$ alkyl or $C_{1-6}$ hydroxyalkyl radical, $C_{1-6}$ alkenyl or $C_{1-6}$ alkynyl radical or form together with the nitrogen to which they are attached, a saturated heterocycle of the class consisting of pyrrolidino, not substituted or substituted by a $C_{1-6}$ alkoxycarbonyl or carboxy group, piperazino, 4-($C_{1-6}$) piperazino, 4-($C_{1-6}$ hydroxyalkyl)piperazino, or piperidino not substituted or substituted by one of the following groups: -$C_{1-6}$ alkyl, benzyl, hydroxy, $C_{1-6}$ hydroxyalkyl, amino, $C_{1-6}$ aminoalkyl, hydroxyamino, $C_{1-6}$ alkoxycarbonyl or carboxy;
Ar represents a phenyl, alpha-naphthyl or beta-naphthyl group, unsubstituted or substituted with a $C_{1-6}$ alkyl or a $C_{1-6}$ alkoxycarbonyl; and their addition salts with pharmaceutically acceptable mineral or organic acids as well as the stereoisomers or their mixture.

2. Compounds according to claim 1, with the formula (I) in which $R_1$ represents hydrogen or a $C_{1-6}$ alkyl radical.

3. Compounds according to claim 1, with the formula (I) in which $R_2$ represents a $C_{1-6}$ alkyl radical.

4. Compounds according to claim 1, with the formula (I) in which the group

represents a piperidino not substituted or substituted with a $C_{1-6}$ alkyl or benzyl.

5. Compounds according to claim 1 with the formula (I) in which Ar represents a naphthyl radical.

6. Compounds according to claim 1, with the formula (I), in which $R_1$ represents hydrogen or a $C_{1-6}$ alkyl radical, $R_2$ represents a $C_{1-6}$ alkyl radical, $NR_3R_4$ represents a piperidino radical and Ar represents a naphthyl radical.

7. 1-[Nα-methyl-Nα-(N-betanaphthylsulphonylglycyl)-p-amidinophenylalanyl]piperidine and its pharmaceutically acceptable salts.

8. 4-methyl-1-[Nα-methyl-Nα-(N-betanaphthylsulphonylglycyl)-p-amidinophenylalanyl]piperidine and its pharmaceutically acceptable salts.

9. 1-[Nα-ethyl-Nα-(N-betanaphthylsulphonylglycyl)-p-amidinophenylalanyl]piperidine and its pharmaceutically acceptable salts.

10. 1-[Nα-ethyl-Nα-(N-betanaphthylsulphonylglycyl)-p-amidinophenylalanyl]-4-methylpiperidine and its pharmaceutically acceptable salts.

11. 1-[Nα-methyl-Nα-(N-betanaphthylsulphonyl-(S)-seryl)-p-amidinophenylalanyl]piperidine and its pharmaceutically acceptable salts.

12. 1-[Nα-methyl-Nα-(N-betanaphthylsulphonyl-(S)-threonyl)-p-amidinophenylalanyl]piperidine and its pharmaceutically acceptable salts.

13. Compound of claim 1 which is 1-[Nα-butyl-N alpha(N-beta-naphthyl-sulphonylglycyl)-p-amidinophenylalanyl]piperidine or a pharmacological active salts thereof.

14. Compound of claim 1 which is 1-[Nα-methyl-N alpha(beta-naphthylsulphonyl-(S)-alanyl)-p-amidinophenylalanyl]piperidine or a pharmacological active salt thereof.

15. Compounds with the formula:

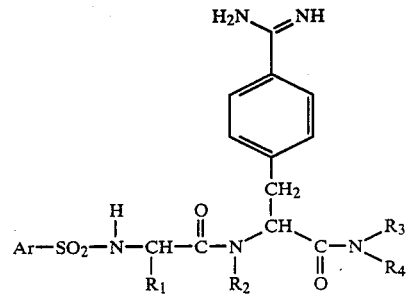

in which:
$R_1$ represents hydrogen, a $C_{1-6}$ alkyl group, $C_{1-6}$ hydroxyalkyl group, a benzyl group, a phenyl group or a 4-hydroxyphenyl group;

$R_2$ represents a $C_{1-6}$ alkyl, $C_{1-6}$ alkenyl, or $C_{1-6}$ alkynyl group, or a benzyl group, or a $C_{1-6}$ alkoxycarbonylalkyl, $C_{1-6}$ carboxyalkyl or $C_{1-6}$ hydroxyalkyl group;

$R_3$ and $R_4$, identical or different, each represents a $C_{1-6}$ alkyl or $C_{1-6}$ hydroxyalkyl radical, $C_{1-6}$ alkenyl or $C_{1-6}$ alkynyl radical or form together with the nitrogen to which they are attached, a saturated heterocycle of the class consisting of pyrrolidino not substituted or substituted by a $C_{1-6}$ alkoxycarbonyl or carboxy group, or piperidino not substituted or substituted by one of the following groups: $C_{1-6}$ alkyl, benzyl, hydroxy, $C_{1-6}$ hydroxyalkyl, amino, $C_{1-6}$ aminoalkyl, hydroxyamino, $C_{1-6}$ alkoxycarbonyl or carboxy;

Ar represents a phenyl, alpha-naphthyl or beta-naphthyl group, unsubstituted or substituted with a $C_{1-6}$ alkyl or a $C_{1-6}$ alkoxycarbonyl; and their addition salts with pharmaceutically acceptable mineral or organic acids as well as the stereoisomers or their mixture.

16. Compounds according to claim 15, with the formula (I) in which $R_1$ represents hydrogen or a $C_{1-6}$ alkyl radical.

17. Compounds according to claim 15, with the formula (I) in which $R_2$ represents a $C_{1-6}$ alkyl radical.

18. Medicament characterized in that it contains, as active principle, a derivative with the formula (I) according to claim 1 or one of its pharmaceutically acceptable salts.

19. Medicament according to claim 18, characterized in that it is presented in the form of unit doses each containing from 0.005 g to 0.500 g of active principle.

* * * * *